United States Patent
Kostrzewa (10) Patent No.: US 9,275,188 B2
(45) Date of Patent: Mar. 1, 2016

(54) MULTI-STAGE SEARCH FOR MICROBE MASS SPECTRA IN REFERENCE LIBRARIES

(75) Inventor: Markus Kostrzewa, Taucha (DE)

(73) Assignee: Bruker Daltonik GmbH, Bremen (DE)

( * ) Notice: Subject to any disclaimer, the term of this patent is extended or adjusted under 35 U.S.C. 154(b) by 1125 days.

(21) Appl. No.: 13/005,863

(22) Filed: Jan. 13, 2011

(65) Prior Publication Data

US 2011/0202282 A1    Aug. 18, 2011

(30) Foreign Application Priority Data

Feb. 1, 2010   (DE) .......................... 10 2010 006 450

(51) Int. Cl.
| | | |
|---|---|---|
| *G06F 19/28* | (2011.01) | |
| *C12Q 1/04* | (2006.01) | |
| *H01J 49/00* | (2006.01) | |
| *G01N 33/68* | (2006.01) | |

(52) U.S. Cl.
CPC  *G06F 19/28* (2013.01); *C12Q 1/04* (2013.01); *G01N 33/6848* (2013.01); *H01J 49/0036* (2013.01)

(58) Field of Classification Search
CPC ......... C12Q 1/04; G06F 19/28; H01J 49/0039
See application file for complete search history.

(56) References Cited

U.S. PATENT DOCUMENTS

| | | | |
|---|---|---|---|
| 4,075,475 A * | 2/1978 | Risby et al. ................... 250/282 |
| 4,885,697 A * | 12/1989 | Hubner .................... C12Q 1/68 324/312 |
| 5,822,219 A | 10/1998 | Chen et al. |
| 6,177,266 B1 * | 1/2001 | Krishnamurthy et al. . 435/173.1 |
| 6,263,334 B1 * | 7/2001 | Fayyad et al. ................. 707/737 |
| 6,513,029 B1 * | 1/2003 | Agrawal et al. ........ 707/999.002 |
| 7,020,559 B1 * | 3/2006 | Demirev .................. C12Q 1/04 702/19 |
| 7,391,017 B2 | 6/2008 | Kostrzewa et al. |
| 2002/0103784 A1 * | 8/2002 | Lee et al. .......................... 707/2 |
| 2005/0044087 A1 * | 2/2005 | Li et al. ......................... 707/100 |
| 2005/0071349 A1 * | 3/2005 | Jordan et al. .................. 707/100 |
| 2005/0142584 A1 * | 6/2005 | Willson et al. ..................... 435/6 |
| 2006/0047696 A1 * | 3/2006 | Larson et al. ............. 707/103 R |

(Continued)

FOREIGN PATENT DOCUMENTS

| | | |
|---|---|---|
| WO | WO 02/25574 A3 | 3/2002 |
| WO | WO 2004/099763 A1 | 11/2004 |

OTHER PUBLICATIONS

Demirev, P. A., Ho, Y.-P., Ryzhov, V. & Fenselau, C. Microorganism Identification by Mass Spectrometry and Protein Database Searches. Anal. Chem. 71, 2732-2738 (1999).*

(Continued)

*Primary Examiner* — Soren Harward
(74) *Attorney, Agent, or Firm* — Benoit & Cote, Inc.

(57) ABSTRACT

Microbes in a sample are identified by calculating similarities between a mass spectrum of the sample and reference mass spectra in a spectral library. The spectral library is divided into a hierarchy of sub-libraries where each sub-library contains reference mass spectra of microbes which are statistically the most prevalent in the samples, but are not included in other sub-libraries and all additional reference mass spectra in the library that have substantial similarity to the reference mass spectra of these microbes. Only if the search in a sub-library does not provide a hit with sufficient certainty of identification, is the search carried out in sub-libraries of higher stages.

8 Claims, 2 Drawing Sheets

(56) References Cited

U.S. PATENT DOCUMENTS

2006/0116984 A1* 6/2006 Zurek .............................. 707/3
2009/0319476 A1* 12/2009 Olston et al. ..................... 707/2

OTHER PUBLICATIONS

Dworzanski, J. P. et al. Mass spectrometry-based proteomics combined with bioinformatic tools for bacterial classification. J. Proteome Res. 5, 76-87 (2006).*

Lay, J. O. MALDI-TOF mass spectrometry of bacteria. Mass Spectrom. Rev. 20, 172-194 (2001).*

Van Baar, Ben; "Characterisation of Bacteria by Matrix-Assisted Laser Desorption/Ionisation and Electrospray Mass Spectrometry"; FEMS Microbiology Reviews; 24 (2000); 193-219; Elsevier.

Jarman, et al.; "An Algorithm for Automated Bacterial Identification Using Matrix-Assisted Laser Desorption/Ionization Mass Spectrometry"; Anal. Chem.; 2000, vol. 72, No. 6, 1217-1223, Mar. 15, 2000.

Keys C J et al: "Compilation of a MALDI-TOF mass spectral database for the rapid screening and characterisation of bacteria implicated in human infectious diseases", Infection, Genetics and Evolution, Elsevier, Amsterdam, NL, vo 1, 4, No. 3, Sep. 1, 2004, pp. 221-242.

Demirev P A et al: "Bioinformatics and mass spectrometry for microorganism identification: proteome-wide post-translational modifications and database search algorithms for characterization of intact H. pylori", Analytical Chemistry, American Chemical Society, US, vol. 73, No. 19, Oct. 1, 2001, pp. 4566-4573.

Logan B et al: "Reducing the cost of 1-11 protein identifications from mass spectrometry databases", Annual International Conference of the IEEE Engineering in Medicine and Biology Proceedings—Conference Proceedings 26th Annual International Conference of the IEEE Engineering in Medicine and Biology Society, EMBC 2004 2004 IEEE, v. 4, Sep. 1, 2004, pp. 3060-3063.

Nagy E et al: "Species identification of 1-11 clinical isolates of Bacteroides by matrix-assisted laser-desorption/ionization time-of-flight mass spectrometry.", Clinical Microbiology and Infection the Official Publication of the European Society of Clinical Microbiology and Infectious Diseases Aug. 2009 LNKDPUBMED: 19438622, vol. 15, No. 8, Aug. 2009, pp. 796-802.

Demirev P A et al: "Mass spectrometry for rapid characterization of microorganisms", Annual Review of Analytical Chemistry 2008 Annual Reviews Inc. USA, vol. 1, No. 1, 2008, pp. 71-93 031207.

* cited by examiner

MULTI-STAGE SEARCH FOR MICROBE MASS SPECTRA IN REFERENCE LIBRARIES

BACKGROUND

The invention relates to the identification of microbes in a sample by calculating the similarities between a mass spectrum of the sample and reference mass spectra in large libraries. The routine fast and error-free identification of many samples of microorganisms plays an important role particularly in clinical and non-clinical infection diagnostics, in hygiene monitoring in hospitals or in rivers and lakes used for swimming, and also in food analysis, monitoring of biotechnological processes or in microbiological research. Microorganisms, here also called microbes for short, include all microscopically small organisms, for example unicellular fungi (e.g. yeasts), algae, or protozoa (e.g. plasmodia as malaria pathogens), although the focus of the identification is usually on bacteria. Viruses are also occasionally categorized as microorganisms, although in the strictest sense they are not true organisms because they have no metabolism.

Identifying microbes basically means determining their species and thus categorizing them in the taxonomic hierarchical scheme: domain (eukaryotes and prokaryotes), kingdom, phylum, class, order, family, genus, and species.

The practice of classifying microorganisms into species originates from a time when taxonomy was largely based on differentiating by means of biochemical reactions and, in many cases, it is imprecise and describes non-uniform phylogenetic units within the microorganisms. The conventional biological definition for distinguishing species from each other by the unlimited sexual reproductive ability of their members among themselves cannot, unfortunately, be applied to microorganisms. Modern methods of molecular biology therefore lead to many corrections in the assignment of species to the genera, and also to the introduction of new species and, in the case of bacteria, additional taxonomic classes below the species, e.g. subspecies. Furthermore, observations in medicine and cell biology have led to the insertion of serovars or serotypes, which are particularly distinguished by different types of attachment behavior at the cell membrane, but which do not constitute a separate species or subspecies. Microorganisms are collected worldwide in many places in the form of frozen or freeze-dried strains.

The identification of a microbe sample within the meaning of this text involves the determination of at least the genus, usually the species, and if possible the subspecies as well, or—in favorable cases—even the serotype or the strain. The strains of one species stored around the world can often be distinguished from each other using molecular biological methods, just as humans are different although they all belong to the same species.

In a more general sense an identification can also mean a characterization in terms of other properties, such as the pathogenicity of a microorganism (ability to cause disease) or the resistance of a microorganism to antibiotics, but this type of identification is only regarded here in a more general sense because many of these characteristics are directly linked, or often have at least a high statistical probability of being linked, with the species, subspecies, serovars or strains. The statistical linkage may even vary from location to location, sometimes from hospital to hospital.

The traditional identification of microorganisms in a sample under investigation requires the cultivation of colonies of the microorganisms. The "API tests" used in laboratory practice comprise different culture media for the cultivation, which can be used to detect specific metabolic characteristics of the microorganisms, thus allowing an initial, usually approximate, taxonomic classification of the microorganisms. Moreover, the microscopic morphology of individual organisms of a colony and the morphology of the colony itself are investigated. On the other hand, new molecular-biological identification methods based, for example, on a DNA or RNA sequence analysis after replication of specific genetic sequences by polymerase chain reaction (PCR), or on mass spectrometric detection of specific molecular cell components of microorganisms, have been known for some years. These new methods are superior to conventional methods in terms of specificity (true-negative rate), sensitivity (true-positive rate), other error rates and analytical speed.

The identification of bacteria by mass spectrometric measurements has been described in detail in the review by van Baar (FEMS Microbiology Reviews, 24, 2000, 193-219: "Characterization of bacteria by matrix-assisted laser desorption/ionization and electrospray mass spectrometry"), for example. The identification is achieved by means of a similarity analysis between a mass spectrum of the bacteria to be identified and reference spectra of accurately known bacteria. During the similarity analysis, a similarity index is assigned to each of the reference spectra. This index characterizes the agreement between the reference spectrum and the mass spectrum of the sample. A bacterium can be classified as identified, for example, if the similarity index is significantly larger than the similarity index for all other reference spectra and also larger than a specified minimum value.

The reference spectra are usually collected in a library, which can contain not only reference spectra of bacteria, but also of other microbes, in order to identify not only bacteria, but also other species of microorganism.

Validation of a library of reference mass spectra requires every entry to be traceable and very accurately documented. The reference spectra are obtained from accurately characterized strains. Such strains of microorganisms are collected worldwide in governmental, public and private institutes, usually stored in the deep-frozen or freeze-dried state, and are available for scientific purposes. Microbiological research institutes frequently hold further strains of newly discovered species of microbe. The exact classification in the taxonomical hierarchy scheme is sometimes disputed, but this does not diminish the value of such strains, as long as the data are traceable. The exact taxonomical classification may be even improved by mass spectrometric means because the similarity indices reflect the relationship of microbe species and their belonging to genera and families.

The term "strain" describes a population which has been propagated from a single organism and identified with certainty in a laboratory of recognized reputation. Spectral libraries are compiled using strains whose identity and classification in the hierarchy system above is accurately known (even if occasionally disputed and subject to changes), i.e. which belong to a certain species of microbe, or, if available, a specific subspecies. Since the microbes are collected and stored in different places worldwide, there are also many strains worldwide which belong to the same subspecies. Although these strains are classified as the same subspecies, there are sometimes slight differences in the mass spectra, which indicate that there are individual differences (as is the case with animals or plants of the same species), such as the serotypes. The strains are marked by internationally agreed labels after the name of the species or subspecies. In contrast to the term "strain", a population which has been grown from a single organism in a microbiological laboratory, e.g. in the process of identification, is termed an "isolate".

The generation of mass spectra of the microbes usually starts with a cleanly isolated colony on a solid, usually gelatinous nutrient medium or a centrifuge sediment (pellet) from a liquid nutrient medium. A small swab, e.g. a wooden tooth pick, is used to transfer a tiny quantity of microbes from the selected colony or sediment to the mass spectrometric sample support. A strongly acidified solution of a conventional matrix substance is then sprinkled onto this sample, the matrix substance serving for a subsequent ionization by matrix-assisted laser desorption (MALDI). The acid of the matrix solution attacks the cell walls and weakens them; the organic solvent penetrates the microbial cells, causes them to burst due to osmotic pressure, and releases the soluble proteins. The sample is then dried by evaporating the solvent, which causes the dissolved matrix material to crystallize. The soluble proteins and to a minor extent other substances of the cell, are embedded into the matrix crystals.

There are borderline cases where the cell walls of the microbes are difficult to destroy or are not destroyed at all by the matrix solution. A slightly different type of digestion is then possible, where in addition to strong acids, sonication or mechanical treatment also helps to destroy the microbial cell wall. These digestions result in mass spectra which are very similar to those prepared in the usual way on sample supports. These digestion methods will not be discussed further here, however. The libraries of reference spectra may contain reference spectra for both preparation methods in parallel.

The sample preparations dried on sample supports, i.e. the matrix crystals with the embedded analyte molecules, are bombarded with pulsed UV laser light in a mass spectrometer, creating ions of the analyte molecules which can then be measured in the mass spectrometer, separated according to the mass of the ions. This type of ionization by matrix-assisted laser desorption is usually abbreviated to "MALDI" ("Matrix-Assisted Laser Desorption and Ionization"). Usually, special MALDI time-of-flight mass spectrometers are used for this purpose.

Nowadays, the mass spectra of the microbe proteins are scanned in the linear mode of these time-of-flight mass spectrometers, i.e. without using an energy-focusing reflector, because this gives a particularly high detection sensitivity, even though the mass resolution and the mass accuracy of the spectra from time-of-flight mass spectrometers are much better in the reflector mode. In the reflector mode, however, only around a twentieth of the ion signals appear, and the detection sensitivity is one to two orders of magnitude worse. The high sensitivity of the linear mode is based on the fact that not only the stable ions but also the charged and neutral fragments from so-called "metastable" decays of the ions are detected in a time-of-flight mass spectrometer. Secondary electron multipliers (SEM) are used to measure the ions, which means that the ion detector measures not only the unfragmented molecular ions and the fragment ions but also the neutral particles, because they also generate secondary electrons on impact. If a singly charged molecular ion fragments into five particles, for example, four of them are by necessity neutral particles. All the fragments that originate from one species of parent ion have the same speed as the parent ions and thus arrive at the ion detector at the same time. The time of flight is a measure of the mass of the originally undecayed ions.

The increased detection sensitivity is so crucial for many applications that one accepts many of the disadvantages of time-of-flight mass spectrometers in linear operation, such as a significantly lower mass resolution and also a reduced mass accuracy. The energy of the desorbing and ionizing laser is increased for these applications, something which increases the ion yield but also increases their instability, although this is of no consequence here.

The poor reproducibility of the desorption and ionization processes for the generation of the ions in a MALDI time-of-flight mass spectrometer operated in linear mode means the masses of the individual mass signals shift slightly from spectrum to spectrum. These shifts in the mass scales of the repeat spectra with respect to each other can be readjusted using a method described in the document DE 10 2004 051 043 A1 (M. Kostrzewa et al.; GB 2 419 737 B; U.S. Pat. No. 7,391,017 B2), before the repeat spectra are combined to produce a reference spectrum. The mass scales of sample and reference spectra can also be aligned with each other by this mass scale adjustment program. This means that smaller mass tolerance intervals can be used to determine matching mass signals during the similarity analysis, which is decisive for a good identification, even if it takes some time.

The mass spectrum of a microbe isolate is the frequency profile of the mass values of the ions. The ions here are predominantly protein ions, in most cases ions of ribosomic proteins. The mass spectra are usually acquired in the mass range from 2,000 to 20,000 atomic mass units; the most useful information for identifications is found in the mass range from around 3,000 atomic mass units to 15,000 atomic mass units. The reduced resolution means the mass signals of the different isotopic compositions of the ions in this mass range are no longer resolved individually; instead, each isotope group forms a single fused mass signal. The protein ions in this method are usually only singly charged (charge number $z=1$), thus we can simply refer to the mass m of the ions here, instead of using the more accurate term of the "charge-related mass" m/z, as is actually necessary and conventional in mass spectrometry. Only occasionally mass signals of doubly charged ions occur in the mass spectra of microbes; but as these mass signals are treated like all the others without any difference whatsoever, there is no need to distinguish between singly and doubly charged ions.

Every laser light pulse produces a single mass spectrum, but one which contains the signals of only a few hundred to a few thousand ions. In order to obtain more reliable and less noisy mass spectra, a few tens to a few hundreds of these individual mass spectra are added together to form a sum mass spectrum. The individual mass spectra here can preferably originate from different parts of the sample preparation or even from different sample preparations. The term "mass spectrum of a microbe", or more simply "microbe spectrum", shall always denote this sum mass spectrum.

The profile of the proteins of this microbe spectrum is very characteristic of the species of microbe in question because each species of microbe produces its own, genetically predetermined proteins, each having their own characteristic masses. The abundances of the individual proteins in the microbes, in as much as they can be measured mass spectrometrically, are also largely genetically determined because their production is controlled by other proteins, and the abundances depend only slightly on the nutrient medium or the degree of maturity of the colony. The protein profiles are characteristic of the microbes in the same way that fingerprints are characteristic of humans.

Reference spectra for spectral libraries are generated by first producing colonies or centrifuge sediments of microbes of specific, accurately documented strains and then acquiring mass spectra from them. A large number of sum mass spectra are always acquired for a reference spectrum; they are termed repeat spectra here. Mass spectra of microbes usually contain around 50 to 200 separate mass signals, but many of them are pure noise because the search for mass signals is set to high sensitivity. The reference spectra are therefore usually reduced to a maximum of 70 or 100 mass signals, for example; specialists consider even a limit of 50 mass signals to be sufficient. The information content of a mass spectrum with 50 mass signals in the mass range between 3,000 and 15,000 atomic mass units, where even at reduced mass resolving power far more than 2,000 distinguishable mass signals can occur, is already incredibly high, without taking account of the intensity differences (close to $2,000^{50} \approx 10^{155}$ patterns can be distinguished from each other). For the restriction to 70 or 100 mass signals, the repeat spectra are initially combined to give an average spectrum very rich in signals before first deleting all mass signals which occur only a few times in the repeat spectra, and then deleting the mass signals with very low intensities until the desirable maximum number of mass signals remains.

The mass spectra of the microbes to be identified, called "sample spectra" below for short, are usually generated in a similar way from repeat spectra and limited to a predetermined number of mass signals in order to exclude noise signals as best as possible. This number of mass signals in these sample spectra is usually selected to be slightly higher than the number of signals in the reference spectra.

There are different types of similarity analysis, which are also usually based on different forms of the reference spectra. The reference spectra can store many or few mass-spectrometric parameters for each mass signal, which has a great impact on the length of the reference spectra and thus on the size of the library.

The publication by Jarman et al., for example, (Analytical Chemistry, 72(6), 2002, 1217-1223: "An Algorithm for Automated Bacterial Identification Using Matrix-Assisted Laser Desorption/Ionization Mass Spectrometry") elucidates a computational method for the generation of reference spectra of a library and for similarity analysis between a mass spectrum of a sample under investigation (called "sample spectrum" here) and the reference spectra of the library. This method particularly utilizes the reproducibility of the individual mass signals when generating the reference spectra. For the similarity analysis of a sample spectrum, the method derives an individual index for every mass signal of every reference spectrum, indicating how well it matches the mass signal of the sample spectrum. Particular attention is paid to the agreement of the intensities, on the one hand, and a weighting resulting from the spread of the reference signals, on the other hand. The smaller the spread of the intensity for this mass signal (i.e. the better this mass signal can be reproduced), the higher this individual weighting index will be. Mass signals which have poor reproducibility receive a low individual weighting index. The individual weighting indices of the mass signals of the reference spectra thus obtained are then summed to derive a similarity index indicating how closely each reference spectrum matches the sample spectrum. The reference spectra in a library are then sorted according to the magnitude of the similarity indices. The result is a list, sorted according to similarities, which contains the designations of the microorganisms assigned to the reference spectra and the similarity indices.

This algorithm according to Jarman et al., which is only outlined here, requires that a reference spectrum contains the following values for the individual mass signals of the reference spectrum, which are ascertained from the repeat spectra: the averaged mass, the mean deviation of the averaged mass, the average intensity, the mean deviation of the average intensity and how frequently this mass signal occurs above background in the repeat spectra, as a percentage, i.e. its occurrence above the sensitivity threshold. It is usual here to taken into account only those signals in a reference spectrum which have a predetermined minimum percentage of occurrence.

In addition to the method by Jarman et al., several other types of identification algorithm and reference libraries have been elucidated in the literature, but they will not be dealt with further here.

As identification methods developed by the applicant's company show, significantly simpler mass spectrometric identification methods can also have a very high success rate. For example, in contrast to the method used by Jarman et al., it is expedient—for the acquisition of both the reference spectra and the sample spectra—if the spectra are generated under standardized conditions for the cultivation of the colony, the sample preparation and the mass spectrometric spectrum acquisition. This measure alone leads to an improved identification. There is then no need to store any of the mean deviations of mass values and intensity values in the reference spectra, which makes the library smaller and more practical, and makes the similarity analysis faster. A method for aligning the mass scales of the repeat spectra with respect to each other, which frequently show a slight mass shift, has already been dealt with above. Since many mass signals occur in only some of the repeat measurements, but can nevertheless contribute to the identification, it has proved expedient in many experiments with reference spectra simplified in this way to also record the occurrence rate of a mass signal. The occurrence rate gives the percentage of the repeat spectra in which this mass signal occurs. A mass signal then only has three entries: averaged mass, averaged intensity and occurrence rate.

In its simplest form, the method for the similarity analysis with these simplified reference spectra can consist in examining every reference spectrum to see how many of its mass signals agree in each case with those of the microbe spectrum within a specified mass tolerance. The number of these hits, divided by the number of mass signals in the reference spectrum is then an initial partial measure for the similarity; the number of hits divided by the number of mass signals in the microbe spectrum is a second partial measure. A third partial measure can be derived from the intensity similarity of the mass signals that agree. The product of the three partial measures gives the similarity index. A refinement can be introduced by counting each hit only with the occurrence rate of this mass signal, i.e. with a number which is possibly less than one.

This algorithm can be adjusted by an appropriate scale transformation to a maximum similarity index between measured and reference spectra, for example a maximum similarity index of 3.00 for identical spectra. It is even possible to transform the similarity indices in such a way that a similarity value of 2.00 can be considered to be a minimum requirement for an identification. In our experience, such a minimum requirement and a corresponding maximum value have a high psychological value for the acceptance of the method.

For this simple similarity analysis it is possible to develop an algorithm which calculates a similarity index for a reference spectrum in around five milliseconds, some of this time being taken up by the mass scale adjustment. An identification with the aid of a sample spectrum in a reference library containing around 3,500 reference spectra, as are available nowadays, requires around 15 seconds on normal computer servers. This time is compatible with acquisition times for the sample spectra which are achieved with pulsed lasers at 20 hertz repetition frequency, but today's mass spectrometers can acquire mass spectra at 1,000 hertz in a much shorter time.

The development of MALDI mass spectrometers is advancing apace; the first spectrometers with a 2,000 hertz laser shot frequency are already on the market. The acquisition time for sample spectra is decreasing to between one and three seconds. On the other hand, one can expect that the libraries will quickly grow to 10,000 reference spectra and more as further reference spectra are entered, while the development of higher speeds for PCs and computer servers is advancing only slowly. The computation times for the identification will therefore rapidly increase to around one minute and will thus no longer be compatible with the acquisition times. One solution (albeit expensive) to the problem consists in equipping mass spectrometers with multi-processor systems. It would, however, be a welcome development if methods for increasing the identification speed were available which, in combination with the simple computer systems currently in use, produce suitably short identification times.

SUMMARY

In accordance with the principles of the invention, the reference library is searched using a multi-stage search that involves an initial search for the most similar reference spectra in a relatively small sub-library of a first stage, which contains only 100 to 300 reference spectra, for example. This sub-library contains the reference spectra of only a few, say three to ten, of the statistically most frequently identified species of microbe. Further in accordance with the principles of the invention, the sub-library also contains all the reference spectra whose similarity with these selected microbe reference spectra is above a similarity threshold, in order that a minimally sufficient identification in the first stage does not prevent a much better identification by a much more similar reference spectrum which is hidden in the sub-library of a higher stage. Only if the search in the sub-library of the first stage does not provide a hit with sufficient similarity is the search continued in sub-libraries of stages higher up in the hierarchy which have been created in an analogous manner, or continued, finally, in the whole library.

The hierarchies of the sub-libraries can be created automatically by suitable software programs. Thereby it is possible to minimize the average time taken for an identification on a laboratory-specific and possibly a sample-type-specific basis by taking into account up-to-date statistics on the microbes in the samples of a laboratory or in certain sample types such as stool, urine or blood, and by selecting the number and size of the sub-libraries.

The hierarchical sub-libraries do not need to be libraries which are stored separately. It is sufficient if the affiliation of a reference spectrum to a sub-library is noted in a field of the reference spectrum that is not subject to the quality assurance for a validation. In particular, it is also possible to create tables containing the addresses of the relevant reference spectra of the individual stages outside the library so as not to complicate the validation of a library. This also makes it possible to use several hierarchies in parallel, for different sample types, for example.

DETAILED DESCRIPTION

Figure 1:
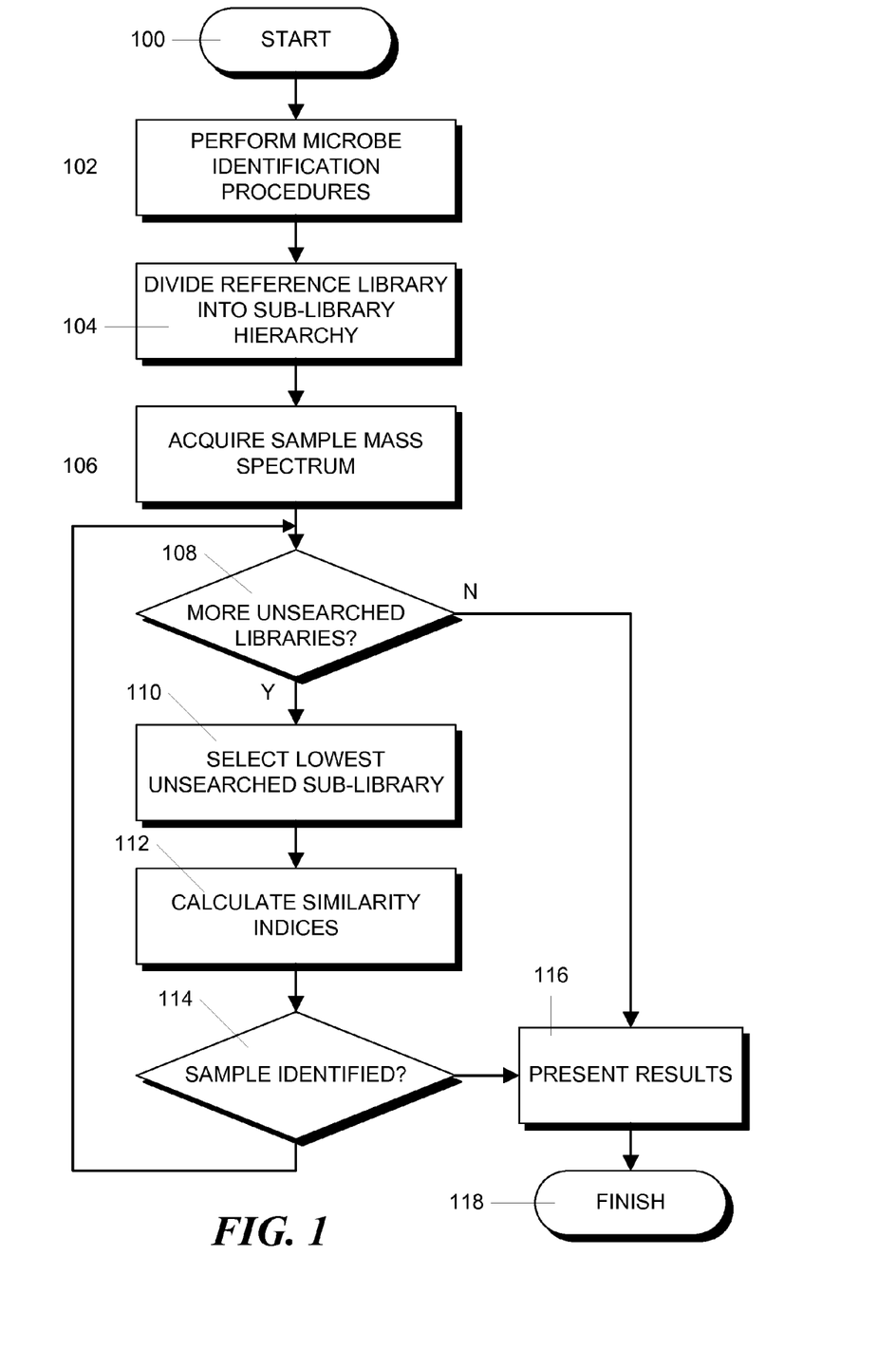
FIG. 1 is a flowchart of the inventive method.

Steps in the inventive method are shown in FIG. 1. This process begins with step 100 and proceeds to step 102 where microbe identification procedures are conducted in order to determine the statistical prevalence of microbes in sample routinely handled by a particular laboratory. Since laboratories routinely perform microbe identification tests by a variety of well-known techniques, this statistical distribution of microbe types may already be known. If not, it can be readily determined.

Then, in step 104, the library of reference mass spectra is divided into a hierarchy of sub-libraries, each of which contains the reference mass spectra of selected microbes. The sub-library at the lowest level of this hierarchy contains the reference mass spectra of the most prevalent microbes in the laboratory and each higher sub-library contains the reference mass spectra of the next most prevalent microbes, etc. This arrangement is illustrated schematically in FIG. 2. The database 200 holds a plurality of records 202. Each record, shown to the left of database 200 in more detail, contains information 204, discussed in detail below, which uniquely identifies the peaks of a mass spectrum of a particular microbe. The records 202 are divided into sub-libraries, of which sub-libraries 208, 210 and 212 are shown. Each sub-library contains records of reference mass spectra of microbes selected for that sub-library. For example, sub-library 208 contains reference mass spectra information 214.

The above-mentioned statistical distribution of microbes among the samples may be different in microbiological laboratories with different specializations. It is then possible to divide the spectra into different sub-libraries by conducting series of similarity calculations, taking into account up-to-date statistics on the prevalence of the microbes in the samples. The average time for the identification can be minimized on a laboratory-specific basis by selecting the number and size of the sub-libraries. The division into sub-libraries can be done automatically using suitable computer programs, overnight for example. The number and size of the sub-libraries for minimizing the identification time can also be selected automatically. The division into sub-libraries can also adapt dynamically to changing identification abundances.

For certain types of sample, such as blood, urine, stool or nasal mucus samples, specific hierarchies of sub-libraries can even be created, because statistically different distributions of microbes are found in these cases. It is also expedient to create different hierarchies of sub-libraries for different fields of application, such as clinical infection diagnostics, or monitoring of food, or monitoring of microbes in rivers and lakes. Similar principles apply to specific analytical methods which are targeted at certain species of microbes, by using special, selective growth media, for example. These analytical methods are often designed only to give the response "positive" or "negative". In these cases, the search can be stopped after the lowest sub-library is searched even in the event of a negative result.

Figure 2:
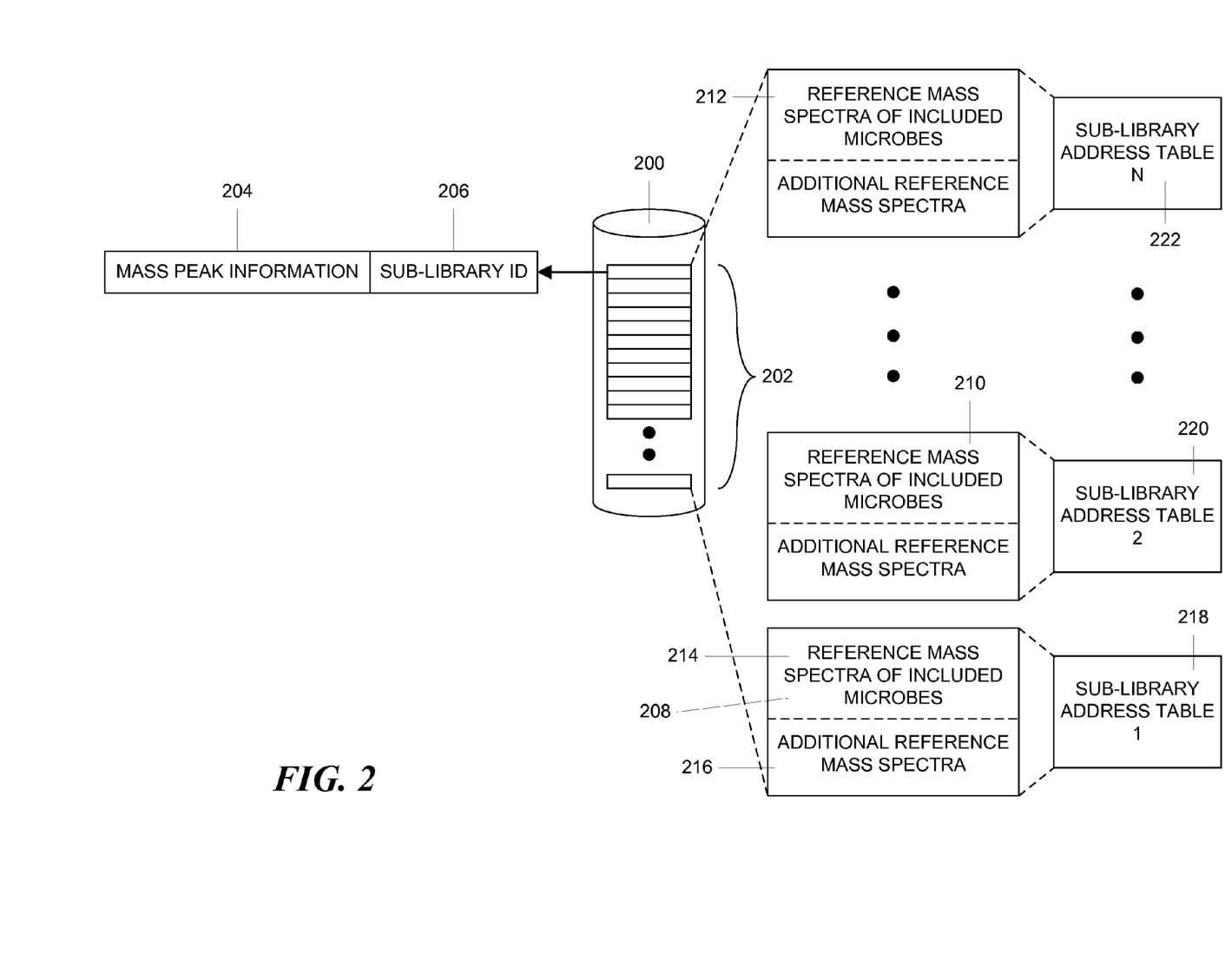
FIG. 2 is a block schematic diagram of a database containing a library of reference mass spectra records and illustrating different method of dividing the library into sub-libraries.

As briefly mentioned before, the invention provides a library of reference spectra 202 divided into hierarchically ordered sub-libraries 208-212 according to the statistical abundances of the microbes as identified in a laboratory, but it is important that each sub-library contain not only the reference spectra of the statistically most frequently found microbes which are not already contained in a lower stage of the hierarchy, but also all reference mass spectra from the library which are not assigned to another sub-library, but have sufficient similarity to the reference spectra of the selected microbes. A reference mass spectrum is considered to have "sufficient similarity" or be "similar" to a reference spectrum of a selected microbe if the calculated similarity index between the two reference mass spectra has a value above a predetermined minimum value. All reference mass spectra that are not assigned to another library, but that are similar to at least one of the reference spectra of the microbes selected for a sub-library, are additionally assigned to that sub-library. For example, sub-library 208 not only contains reference mass spectra of microbes selected for that sub-library 214, but also additional reference mass spectra 216 that are similar to the mass spectra of the selected microbes 214.

If all reference spectra of the microbe species are entered for which a sufficiently similar reference spectrum was found, this ensures that, for an identification hit in a sub-library, the best identification by the most similar reference spectrum can also immediately be found. There cannot be a more similar reference spectrum in sub-libraries of higher stages.

If the analysis of the similarities between all reference spectra and the reference spectra of the microbes selected for a particular sub-library reveals a sufficiently similar spectrum of a microbe species which is not among the selected microbes, it is expedient to also enter all reference spectra of this microbe species into the sub-library, even if not all these reference spectra have sufficient similarity. Of course, then all reference spectra with sufficient similarity to these added reference spectra of the added species should be added, too. This procedure may lead to sub-libraries which are too large. To avoid these too large sub-libraries, it is also possible to include only the sufficiently similar reference spectra of other microbe species; if, however, the similarity search produces a best hit with one of these added similar reference spectra, the similarity search is then continued in the sub-library of a higher stage in the hierarchy containing the other reference spectra of this species or genus. If only single reference spectra of sufficient similarity are added, the threshold for the sufficiency of the similarity index may be lowered.

A non-limiting example of a hierarchy of the sub-libraries prepared for a typical laboratory for medical microbiology is described below. In this laboratory conventional microbe identification procedures confirm that statistically almost 50 percent of all samples to be identified are concerned with only four different species of microbe (*Escherichia coli, Staphylococcus aureus, Staphylococcus epidermis, Pseudomonas aeruginosa*). Consequently, the sub-libraries are designed so that the lowest sub-library in the sub-library hierarchy contains the reference spectra of these four species of microbe and, additionally, all reference spectra of the whole library which are sufficiently similar to one of these reference spectra of these four microbe species. Although the sub-library contains the reference spectra of closely related microbe species, of microbes of different strains of the same species, including the serovars, and also coincidentally similar reference spectra of unrelated microbes, it nevertheless contains only around one hundred reference spectra. The search in this sub-library of the lowest stage takes a mere half a second or so. This means that 50 percent of the samples in this laboratory can already be identified by computation in half a second in each case. The identification can go down to the subspecies or serovar level, especially if the method for the improved identification of microbes with very similar reference spectra is used, which is described in DE 10 2009 032 649 A1 (T. Mayer and M. Kostrzewa, 2009). This application is hereby incorporated herein in its entirety by reference.

Further sub-libraries of higher hierarchical stages can be created in analogy with the lowest stage in terms of content and size so that the average computing time for identification assumes a minimum. For example, a further 25 percent of all samples in the selected laboratory for medical microbiology were made up of only a dozen further species of bacteria (*Klebsiella pneumoniae, Enterobacter cloacae, Staphylococcus hominis, Klebsiella oxytoca, Proteus mirabilis, Candida albicans, Stenotrophomonas maltophilia, Enterococcus faecium, Enterococcus faecalis, Staphylococcus haemolyticus, Candida glabrata, Candida krusei*). The next lowest sub-library containing the reference mass spectra for these microbes contains around 300 reference spectra by including all similar reference spectra. This sub-library can be searched in computing times of around 1.5 seconds so that a total of two seconds or so (including a fruitless search in the sub-library of the lowest stage) is required for an identification of one of these microbes. Three quarters of all identifications can therefore be concluded in 0.75 seconds on average (=½×0.5+¼×2 seconds).

By creating further sub-libraries it is possible to reduce the average computing time for an identification to a total of a few seconds, even if occasionally (preferably in far less than one percent of cases) the complete remainder of the library needs to be searched. If the complete remainder of the library needs to be searched in one percent of the cases, and if this search takes a full minute, the average computation time per identification increases by only 0.6 seconds due to this part of the identity search.

The sub-libraries do not need to be libraries which are stored separately in database 200. In a large library it is sufficient if the affiliation of a reference spectrum to a sub-library is noted in a field of the reference spectrum that is not subject to the quality assurance for a validation, for example field 206 of a library record. However, since the validation of a reference spectrum library must be viewed as very critical, it is much better to create tables containing the addresses of the reference spectra for the sub-libraries of the individual stages outside the library. These tables are shown schematically as address tables 218, 220 and 222 which contain the addresses of the records 202 contained in sub-libraries 208, 210 and 212, respectively. Of course, address tables 218, 220 and 222 may also be stored in database 200. A reference spectrum can thus belong to two or more sub-libraries of different stages, if this should be necessary because of similarities. It is thus also possible to store different hierarchies of sub-libraries for a whole library, for example different hierarchies for different sample types.

In order to perform the inventive method, a library of reference spectra must first be created. Standardized cultivation methods and also standardized methods of spectrum acquisition should be used: precisely specified methods for the cultivating the microbes of accurately known strains, sampling tiny but exactly reproduced quantities of microbes, preparing, for example, at least five samples of each microbe on a mass spectrometric sample support, and acquiring, for example, at least five mass spectra from each of the samples. Each mass spectrum is summed from a specified number of individual spectra. In accordance with the examples stated, at least 25 repeat mass spectra will be obtained for each microbe strain and their acquisition in a suitable mass spectrometer only takes a total of one to two minutes. The large number of repeat spectra is only necessary because the preparation processes of the sample with crystallization of the matrix substance and ion formation by MALDI have only moderately good reproducibility and only produce good reference spectra by averaging over many mass spectra. A large number of repeat spectra also provides more reliable values for the occurrence rates of the mass signals.

Since the desorption and ionization process for the generation of ions in a MALDI time-of-flight mass spectrometer in linear mode can slightly shift the masses of the individual mass signals from spectrum to spectrum, the mass scales of the repeat spectra are now adjusted with respect to each other using a method already cited at the beginning, which is elucidated in the patent application DE 10 2004 051 043 A1 (M. Kostrzewa et al.), which application is hereby incorporated by reference in its entirety. This means smaller mass tolerance intervals can be used for determining the hits as described below, for example 250 instead of 1,000 millionths of the mass (ppm). This adjustment of the mass scales means a decisive improvement for the method.

As previously mentioned, a simple type of reference mass spectra, which records only mass, intensity and occurrence rate for each mass signal is used because the associated, very easy method of calculating similarity indices is very fast and nevertheless leads to outstanding identification results. In particular, once the repeat spectra have been adjusted with respect to each other, the average mass values, the average intensities and the occurrence rates are automatically derived for every mass signal. The occurrence rate indicates how often a mass signal occurs in the repeat spectra; the value is therefore 1.00 (=100%) if this mass signal can be found in all the repeat spectra, and correspondingly smaller otherwise. The reference spectrum produced by combining all the repeat spectra is then restricted to a maximum of 70 mass signals by removing all mass signals below a specified threshold for the occurrence, 15% for example, and by removing the mass signals with the smallest intensities. In a few cases there will be fewer than 70 mass entries in a reference spectrum if, after removing the noise signals, which are characterized by low occurrence, fewer than 70 mass signals remain.

In addition to the mass average, the intensity average and the occurrence rate, each reference spectrum record contains the exact designations of the microbe species, subspecies, and strain corresponding to the entered mass signals. The reference spectrum can also contain several numerical values which are repeatedly needed for the calculation of the similarity indices, for example the number of all mass signals, weighted with the occurrence rate. Moreover, the reference spectra can contain references to the origin of the strains and the laboratory which acquired the spectra, as is required for validations. References to a special pathogenicity of the microbes, the environmental harm they can cause in rivers and lakes, their toxicity in food, their harmfulness in bioprocesses and so on can also be included, preferably in a coded form which can, if required, also be used for an automatic check to establish whether a more detailed identification is necessary. Information on how to treat pathogens or environmental hazards with corresponding encodings can also be included.

In step 106, the inventive method for identification of a microbe sample involves first cultivating the sample to form a colony using the same standardized method as for reference spectra. Microbes from an isolate are transferred onto the sample carrier, prepared with matrix solution and measured in the mass spectrometer. Here, too, it is expedient to measure several mass spectra and combine them in a similar way to the reference spectra to give an averaged mass spectrum, which is here called "sample spectrum". The sample spectrum is restricted to a maximum of 100 mass signals, for example.

The inventive method then proceeds to step 108 to determine whether more unsearched libraries exist. If so, then the process proceeds to step 110 where the lowest unsearched library is selected for a search.

As shown in step 112, the search involves calculating the indices for the similarity of the sample spectrum to each reference mass spectra of the selected sub-library. The simple calculation method for these similarity indices, which has already been briefly described at the beginning and which will serve as an example here, is based on three partial measures: a first partial measure of the similarity index is represented by the number of mass signals in the sample mass spectrum and reference mass spectrum that match within a mass tolerance interval ("hits"), divided by the number of the mass signals in the reference spectrum. All the mass signals are, however, only counted on a pro-rata basis in terms of their occurrence rate. The mass tolerance interval can be stated in absolute terms in atomic mass units (or atomic mass units) or as a relative value in ppm (parts per million). A mass tolerance interval of 250 ppm has proven to be advantageous.

A second partial measure is derived from the number of hits divided by the number of mass signals in the sample spectrum, again with the option of counting them pro-rata with the occurrence rates. The first and second partial measures can each assume a maximum value of 1.00. The third partial measure is calculated from the similarity between the respective intensities of the matching mass signals, with the occurrence rates again being taken into account multiplicatively. This third partial measure is normalized for all mass signals so that when all intensities are equal, the partial measure assumes the value 1.00.

These three partial measures are now simply multiplied with each other to give the index for the similarity between a reference mass spectrum and the sample mass spectrum. Since each of the three partial measures can have a maximum value of 1.00, the similarity index can also have a maximum value of 1.00.

Thousands of verified identifications made by this type of similarity calculation have now shown that a reliable identification is practically always linked to a similarity value greater than 0.10. In order to derive more convenient numbers, the values can be transformed by multiplying by 1,000 and subsequently taking the logarithm, which results in a maximum similarity index of 3.00 for identical spectra and a minimum required similarity index of 2.00 for identification of a species. This transformation is not essential, its value is merely psychological, and as remarked above; any other transformations can therefore also be applied if they prove to be more manageable.

This procedure for calculating the similarity indices can be implemented in a very rapid algorithm; modern computers for use with mass spectrometers take around five milliseconds for the scale adjustment and calculation of each similarity index.

In step 114, the similarity indices are used to perform an identification. The results of the calculations in step 112 are usually presented in a list, where the most similar reference spectra are displayed, ordered according to the similarity indices, with the names of the corresponding microbe species, subspecies and strains. It has been shown that similarities between microbe spectra reflect their relationship. Thousands of verified identifications have shown that similarity indices between 1.70 and 2.00 identify at least the genus, and between 2.00 and 2.30 the species, with certainties of more than 95 percent. Similarity indices above 2.30 even identify individual strains with similarly high certainty. Multidimensional similarity studies for microbes can reveal their position in taxonomical classification schemes.

If the search of the sub-library stage finds similarities of more than 2.00, the microbe species can be assumed to be identified and the results are presented in step 116. The process then ends in step 118. Usually, several reference spectra belonging to the same species are found in the list of the best similarities. They can be used to assess the identification accuracy: if, for example, the best six reference spectra all belong to the same microbe species, and if there are only seven reference spectra of this microbe species in the library, the identification can be categorized as a "high confidence identification", even if the highest similarity index is only slightly above 2.00. These and similar categorizations assist the staff in routine laboratories with their decisions on reliable identifications.

If, however, in the search of the lowest sub-library in the hierarchy the sample cannot be identified—no reference spectrum is found which has a similarity index greater than 2.00—the process proceeds back to step 108 where a determination is made whether unsearched—sub-libraries exist. If so, the search is continued in the lowest unsearched sub-library. In the event of a negative result, the search in sub-libraries of higher stages can be continued until a satisfactory identification has been achieved in step 114 or no further unsearched sub-libraries exist as determined in step 108. In either case, the results are presented in step 116 and the process terminates in step 118. If the highest similarity index was found for an added reference spectrum in a particular sub-library, a search may be tried in a sub-library containing other reference spectra of that species.

If no reference spectra at all are found in the whole library with similarity indices above 2.00, but indices between 1.70 and 2.00 are found, an identification of the genus can be assumed without having achieved an identification of the microbe species. There is then a high probability that the library of the reference spectra does not contain a reference spectrum for this microbe species, which must happen repeatedly given the millions of mostly unknown microbe species. When creating libraries of reference spectra, however, the aim is to at least cover all genera of microbes relevant for the research or routine labs identifying microorganisms. At present, libraries are available comprising reference spectra of all species of known pathogenic microbes.

The multi-stage search can lead to problems if the sample spectra do not originate from pure cultures, i.e. from isolates, but from mixed cultures, even if these mixed cultures consist of only two, or at most three, species of microbe. These mixed cultures can occur when, for example, highly infected blood cultures from patients with serious sepsis are analyzed directly after only a short cultivation because time is of the essence, without further cultivation of clean colonies in Petri dishes. In the vast majority of cases, only one microbe species is found in these blood cultures, but occasionally two or more microbe species can occur. DE 10 2009 033 368.1 (T. Mayer, 2009) describes a corresponding analytical method for such mixed cultures, and DE 10 2009 007 266.7 (M. Kostrzewa et al. 2009) elucidates a computational identification method. Both of these application are hereby incorporated in their entirety by reference. These methods can also be applied here if a sub-library contains microbe species which can occur together in certain samples. If this is not the case for a sample, there is still the difference method also described in the latter document.

With knowledge of the invention, the methods described here can be modified in a variety of ways by the specialist skilled in the art. Some of these variations have already been indicated at above, but there are further methods which can be performed on the fundamental basis of a two-stage or multi-stage identification according to this invention.

While the invention has been shown and described with reference to a number of embodiments thereof, it will be recognized by those skilled in the art that various changes in form and detail may be made herein without departing from the spirit and scope of the invention as defined by the appended claims.

What is claimed is:

1. A method for the identification of an unknown microbe sample by calculating similarity indices between a mass spectrum of the microbe sample and reference mass spectra contained in a library of reference mass spectra, comprising:
    (a) performing microbe identification procedures to determine an identification abundance of each microbe having a reference mass spectrum in the library;
    (b) dividing the library into a hierarchy of sub-libraries, wherein
        a highest sub-library contains reference mass spectra of microbes with an identification abundance that exceeds a predetermined abundance value, and additionally contains all reference mass spectra whose identification abundances fall below the predetermined value, but that have a sufficient similarity to the reference mass spectra with an identification abundance that exceeds the predetermined abundance value and;
        at least one lower sub-library contains reference mass spectra of microbes that have an identification abundance that exceeds additional predetermined abundance values and that are not included in any higher sub-libraries, and additionally contains all reference mass spectra whose identification abundances fall below the additional predetermined abundance values, but that have a sufficient similarity to the reference mass spectra in the at least one lower sub-library;
        wherein an additional reference spectrum is sufficiently similar to a reference spectrum in a sub-library if a similarity index calculated in a similarity analysis between the two reference spectra has a value above a predetermined similarity value;
    (c) acquiring a sample mass spectrum of the microbe sample;
    (d) calculating a similarity index between the sample mass spectrum and each of the reference mass spectra and the additional reference mass spectra in the highest sub-library;
    (e) using the similarity indices calculated in step (d) to determine whether the microbe sample is positively identified, wherein the additional reference spectra in the highest sub-library ensure that, in case of a positive identification, the best identification is found by a reference mass spectrum that is most similar to the sample mass spectrum; and
    (f) if the microbe sample is not positively identified in step (e), repeating steps (d) and (e) with reference mass spectra in a next lower sub-library until either the microbe sample is positively identified or the entire library of reference mass spectra is searched.

2. The method of claim 1, wherein, in step (a), microbe identification procedures are one of measurements conducted in a particular laboratory, measurements of a particular sample type and measurements made with a particular measurement procedure.

3. The method of claim 1, wherein, in step (b), each sub-library additionally contains all reference mass spectra of microbes of the same species as microbes corresponding to the additional reference mass spectra.

4. The method of claim 1, wherein, in step (e), if a calculated similarity index between a single additional reference mass spectrum and the sample spectrum has the highest value of all similarity indices calculated in step (d), but the sample microbe cannot be positively identified, repeating steps (d) and (e) in a sub-library that contains reference mass spectra of microbes of the same species or the same genus of the species of the microbe having the single additional reference mass spectrum.

5. The method of claim 1 wherein step (b) is performed automatically by a computer program using known statistical identification abundances.

6. The method of claim 1, further comprising selecting the number and size of the sub-libraries so as to minimize the average time for said identification.

7. The method according to claim 1, wherein step (b) is re-performed when the identification abundances determined in step (a) change.

8. A method for the identification of a microbe sample by calculating indices for the similarity between a mass spectrum of the microbe sample and reference spectra in a library of reference spectra, comprising the steps of:
 a) providing a library of reference spectra divided into sub-libraries according to the abundance of microbes found statistically in past identification procedures, the first sub-library containing reference spectra of selected microbes with the highest identification abundance and reference spectra which exceed a preset similarity to the reference spectra of the selected microbes;
 b) acquiring a sample mass spectrum of the microbe sample;
 c) searching for similarities with the reference spectra in the first sub-library by calculating a similarity index between the sample mass spectrum and each of the reference mass spectra in the highest sub-library; and
 d) ending the similarity search if a positive identification is available by the search in the first sub-library, otherwise continuing the similarity search by repeating step (c) in sub-libraries with reference spectra of microbes of lower identification abundances.

* * * * *